United States Patent [19]

Miyake et al.

[11] Patent Number: 4,537,763
[45] Date of Patent: Aug. 27, 1985

[54] PRODUCTS SWEETENED WITH α-GLYCOSYL GLYCYRRHIZIN

[75] Inventors: Toshio Miyake; Hiromi Hijiya, both of Okayama, Japan

[73] Assignee: Kabushiki Kaisha Hayashibara Seibutsu Kagaku Kenkyujo, Okayama, Japan

[21] Appl. No.: 387,651

[22] Filed: Jun. 11, 1982

[30] Foreign Application Priority Data

Jun. 20, 1981 [JP] Japan ................... 56-95714

[51] Int. Cl.³ .................. A61K 7/16; A23L 1/236; C12P 19/18; C07H 3/00
[52] U.S. Cl. .................. 424/49; 426/548; 426/549; 426/590; 426/650; 426/660; 426/658; 426/804; 435/97; 536/18.1; 424/64
[58] Field of Search .............. 426/18, 48, 49, 52, 426/548, 655, 804, 658; 435/97; 424/180, 283; 536/18.1; 542/402

[56] References Cited

U.S. PATENT DOCUMENTS

| | | |
|---|---|---|
| 3,878,191 | 4/1975 | Fukumoto et al. ............. 426/548 |
| 3,923,598 | 12/1975 | Horikoshi . |
| 3,988,206 | 10/1976 | Shiosaka . |
| 4,135,977 | 1/1979 | Horikoshi . |
| 4,219,571 | 8/1980 | Miyake ............................ 426/48 |
| 4,393,200 | 7/1983 | Miyashita et al. ............. 536/18.1 |

FOREIGN PATENT DOCUMENTS

| | | |
|---|---|---|
| 49-7227 | 2/1974 | Japan . |
| 57-3659 | 3/1982 | Japan ............................ 426/548 |
| 57-6266 | 5/1982 | Japan ............................ 426/52 |
| 1390065 | 4/1975 | United Kingdom . |

OTHER PUBLICATIONS

Inglett, George E.; *Symposium: Sweeteners*, AVI Publishing Co., Inc., Westport, Conn., 1974, Chs. 19 & 20.
*Chemical Abstracts*, 57000t, vol. 83, p. 359 (1975).
Bender, H., "Cyclodextrin–Glucanotransferase von *Klebsiella pneumoniae*", *Arch. Microbiol.*, 111, pp. 271, 282 (1971).

*Primary Examiner*—Raymond N. Jones
*Assistant Examiner*—Elizabeth C. Weimar
*Attorney, Agent, or Firm*—Browdy and Neimark

[57] ABSTRACT

New α-glycosyl glycyrrhizins bearing two or more α-glucose residues are prepared. Such α-glycosylation is carried out by subjecting an aqueous solution of glycyrrhizin (or a salt thereof) and an amylaceous substance (e.g. starch or cyclodextrin) to the enzymatic action of an α-glycosyl transferase (e.g. cyclodextrin glucanotrasferase). The α-glycosyl glycyrrhizins are low-caloric, low-cariogenic, mild, non-bitter, non-lingering sweeteners which may be advantageously incorporated into foods, beverages, cosmetics, dentifrices and drugs.

13 Claims, 1 Drawing Figure

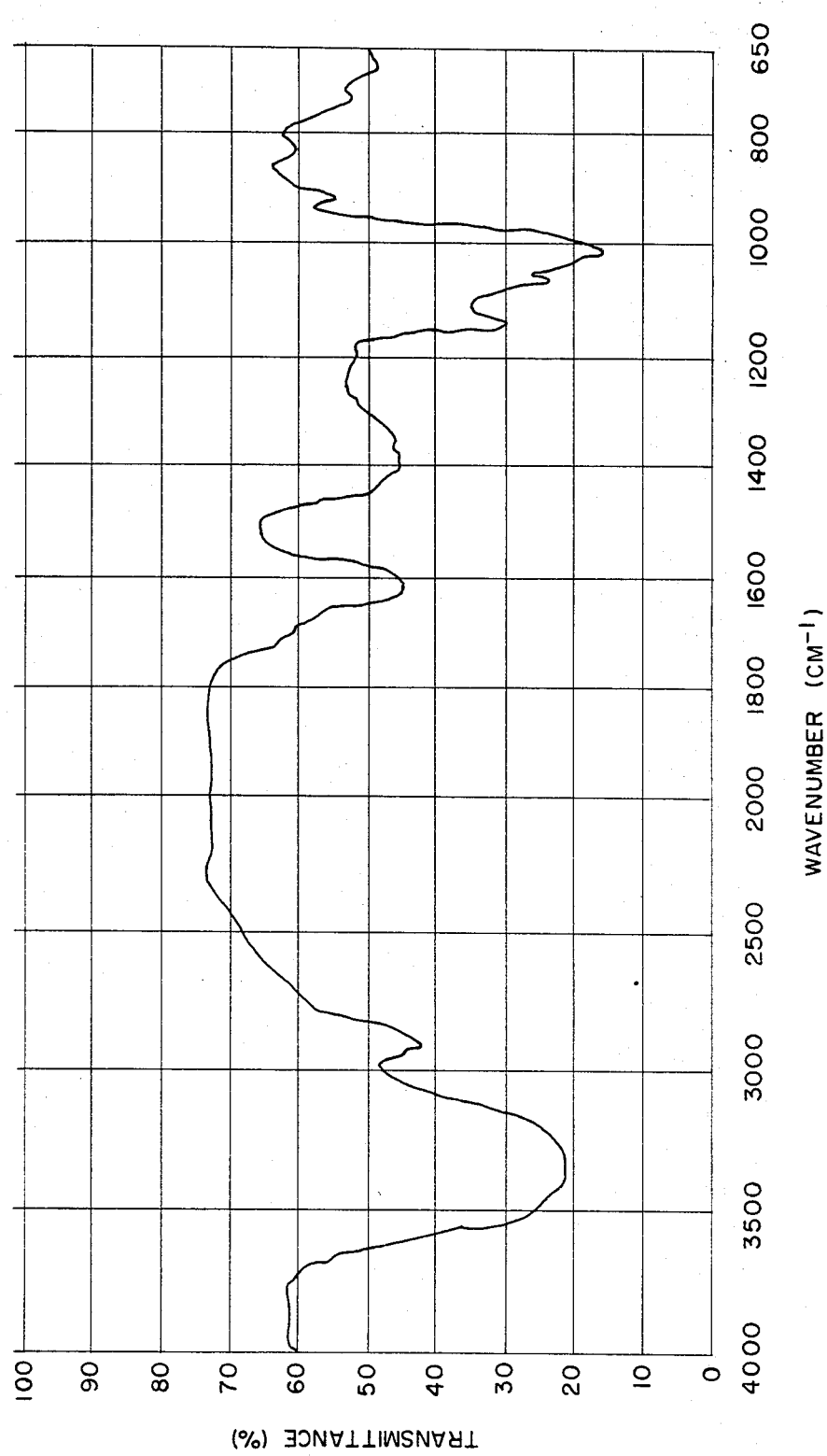

PRODUCTS SWEETENED WITH α-GLYCOSYL GLYCYRRHIZIN

DETAILED DESCRIPTION OF THE INVENTION

The present invention relates to a process for producing food products, characterized in that said food products are prepared with, or include as an additive, α-glycosyl glycyrrhizin.

Also, the invention provides a process for producing food products, characterized in that said food products are prepared with, or include as an additive, α-glycosyl glycyrrhizin which is obtainable by subjecting an aqueous solution, containing glycyrrhizin and amylaceous substance, to the action of cyclodextrin glucanotransferase (E.C. 2.4.1.19).

Glycyrrhizin is a sweet substance, obtained by subjecting root and/or stolon of a perennial plant, Licorice (*Glycyrrhiza glabra* Linne var. *glandulifera* Regal et Herder or *Glycyrrhiza uralensis* Fishey) of family Leguminosae, to an extraction with water, whose molecular structure is of the following glycyrrhizic acid or glycyrrhizinate, which has been widely used as a sweetener from the ancient history.

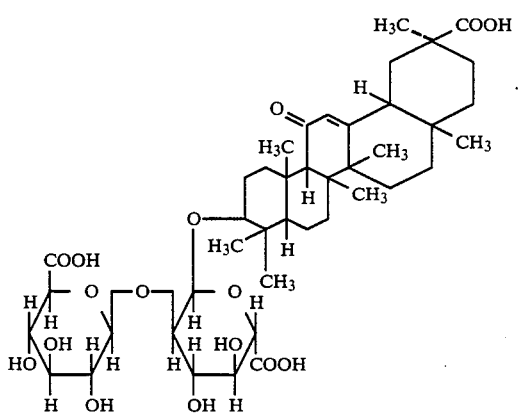

In comparison with other sugar sweeteners, e.g., sucrose, glycyrrhizin has the following disadvantages:

(1) the sweetness of intact glycyrrhizin can not be enjoyed because its additional unpleasant bitter-, astringent-, and harsh tastes and medicinal odor mask the sweetness, (2) oral ingestion of glycyrrhizin is frequently unpleasant because the manifestation of the sweetness of the substance is much more delayed than that of sucrose, and lingers together with the above unpleasant tastes to give an undesirable after-taste, (3) since sedimentation and/or gelatinization of glycyrrhizin in an aqueous solution is effected when the solution is on an acidic side, it is hardly usable in low-pH foods, limiting its use in condiments, and (4) handling of glycyrrhizin in an aqueous solution is troublesome because the agitation, concentration and/or boiling up of the solution sometimes require use of an anti-foaming agent.

In order to overcome the above disadvantages of the glycyrrhizin sweeteners, various attempts have been disclosed in previous patent applications. For example, Japan Patent Publication No. 7,227/74 discloses a method for improving the taste quality of glycyrrhizin with the use of an admixture of glycyrrhizin and sodium citrate in an amount of 30–500% against the former; Japan Patent Publication No. 17,721/68 discloses a method for preventing sedimentation and/or gelatinization of glycyrrhizin under acidic conditions, comprising admixing alkali metal salts and starch hydrolysate to an aqueous solution of Licorice extract, and heating the resultant mixture solution; and Japan Kokai No. 29,777/75 discloses that the use of glycyrrhizin in combination with gluconic δ-lactone and alkali metal salts in food products is preferable for preventing sedimentation and/or gelatinization of glycyrrhizin upon its use under acidic conditions.

All attempts disclosed in these patent applications have, however, proved unsatisfactory in view of taste quality improvement.

In order to eliminate the above described disadvantages of glycyrrhizin and also to help it to find various uses in sweetening food products and improving their taste qualities, the present inventors have investigated various processes.

The efforts resulted in the finding that unlike intact glycyrrhizin, a sweetener prepared with, or added with α-glycosyl glycyrrhizin, wherein one or more α-glucosyl residues are linked to the glycyrrhizin residue in an α-fashion, has the following desirable features:

(1) a mild taste without any undesirable taste or medicinal odor,
(2) a non-lingering taste due to rapid expression of sweetness,
(3) an extreme suppression of sedimentation and/or gelatinization under acidic conditions, and
(4) an easy handling due to extreme suppression of its foamability, as well as in the additional finding that the α-glycosyl glycyrrhizin is advantageously feasible in various food products to sweeten them and also to improve their taste qualities, which led to the present invention.

In addition to foods and drinks in general, the term "food products", as used in the SPECIFICATION, includes all products wherein taste is an important factor, e.g., drinks, such as liquors and soft drinks; foods, such as seasonings, confectioneries, pickles and pickled products; feeds, pet foods; cosmetics, such as lipstick, lipcream and dentifrice; and drugs, such as those for internal administration, gargle.

As to the α-glycosyl glycyrrhizin usable in the invention, any α-glycosyl glycyrrhizin product can be used regardless of its production process so far as it contains α-glycosyl glycyrrhizin wherein one or more α-glucosyl residues are bound to the glycyrrhizin moiety.

As a process for producing the α-glycosyl glycyrrhizin on an industrial-scale, a process which comprises subjecting an aqueous solution, containing glycyrrhizin and amylaceous substance, to the enzymatic action of α-glycosyl transferase, preferably, cyclodextrin glucanotransferase (E.C. 2.4.1.19), is preferable because the process enables an industrial-scale production of α-glycosyl glycyrrhizin at a low-cost.

The following descriptions explain the process in more detail.

As to the glycyrrhizin which is subjected to an enzymatic step using cyclodextrin glucanotransferase, it may be one of those which contains glycyrrhizic acid and/or its salt derivative(s), and gives the α-glycosyl glycyrrhizin by the enzymatic action. Accordingly, a crude glycyrrhizin extract, obtained by extraction from Licorice, is also usable in the process, as well as a highly-purified product with high glycyrrhizin content.

The amylaceous substances usable in the process are those which act as a substrate for the enzyme, and one or more α-glucosyl residues thereof are transferred to the glycyrrhizin residues by the enzymatic action to form the objective α-glycosyl glycyrrhizin. Generally, cyclodextrin, and starch hydrolysates whose Dextrose Equivalent (D.E.) is 1-50, e.g., liquefied starch and saccharified starch, are feasible in the process, as well as amylose, amylopectin and starch.

The starch material may be tuberous or subterranean stem starch from potato or sweet potato; cereal starch from rice, wheat or corn; or that in the crude extract from Licorice.

As disclosed in previous patent applications, e.g., Japan Kokai No. 20,373/72, Japan Kokai No. 63,189/75 or Japan Kokai No. 88,290/75, or as reported by Hans Bender, *Arch. Microbiol.*, Vol. 111, pp.271-282 (1977), it is well documented that cyclodextrin glucanotransferase is produced by a microorganism of genus Bacillus, e.g., *Bacillus macerans, Bacillus megaterium, Bacillus circulans, Bacillus polymyxa,* or *Bacillus stearothermophilus,* or that of genus Klebsiella, e.g., *Klebsiella pneumoniae,* which are all advantageously feasible in the process.

In the process, the cyclodextrin glucanotransferase is not necessarily purified prior to the use, and the objectives are generally attainable with the use of a crude enzyme.

The enzymatic step can be repeatedly carried out continuously or in batches with the use of an immobilized cyclodextrin glucanotransferase.

Employable reaction conditions are those under which the cyclodextrin glucanotransferase acts on the glycyrrhizin and amylaceous substance in an aqueous solution. Generally, glycyrrhizin and amylaceous substance are dissolved together in water to give concentrations of about 0.1-25 w/w % and about 1-50 w/w % respectively, and also to give a preferable weight ratio of amylaceous substance versus glycyrrhizin of about 0.5-500.

As to the reaction pH and temperature applicable for the enzymatic reaction, any pH and temperature can be employed so far as the cyclodextrin glucanotransferase acts on the substrates thereunder to form the α-glycosyl glycyrrhizin. Generally, a pH in the range of 3-10 and a temperature in the range of 20°-80° C. are preferable.

When the extraction of glycyrrhizin is carried out in an aqueous solution containing amylaceous substance, glycyrrhizin may be extracted in a high yield with relatively less contamination of impurities, and the resultant extract may be readily subjected intact, or, if necessary, after concentration, to the enzymatic action of cyclodextrin glucanotransferase to produce the objective α-glycosyl glycyrrhizin.

In this case, the presence of cyclodextrin glucanotransferase in the extract further accelerates the glycyrrhizin extraction, and effects the enzymatic reaction simultaneously, shortening the time required for the extraction and subsequent enzymatic reaction.

The practice of the above described processes enables a direct production of α-glycosyl glycyrrhizin from Licorice with less contamination of impurities.

When the enzymatic action of cyclodextrin glucanotransferase on the substrates leads to the formation of α-glycosyl glycyrrhizin having a high molecular weight α-glycosyl residue, the latter may be, if necessary, subjected to the enzymatic action(s) of other enzyme(s), e.g., α- and/or β-amylase(s), to convert it into an α-glycosyl glycyrrhizin having a lower molecular weight α-glycosyl residue prior to the use, improving its viscosity and taste quality.

Dependent upon the species of food products, the resultant reaction mixture may be used as a sweetener intact, or, if necessary, after purification. For example, after inactivation of the enzymatic activity present in the reaction mixture by heating, the mixture may be treated with an $SiO_2 \cdot Al_2O_3 \cdot MgO$ powder, e.g., "Neucillin", Registered Trade Mark of Fuji Chemical Industry Incorporation, Limited, Toyama-ken, Japan, or magnesium oxide powder, e.g., "M-511", a product of Hokkaido Soda Company, Limited, Tokyo, Japan, both to adsorb and to remove the impurities, and the non-adsorbed part is harvested to obtain a liquid sweetener, which may be, if necessary, prepared into syrup- or powdered sweetener.

The sweetener thus obtained may be further subjected to a purification step using an ion exchanger of H-form to deionize the α-glycosyl glycyrrhizin.

If separation of the sweetener into glycyrrhizin compounds including α-glycosyl glycyrrhizin, and free saccharides is desirable, it can be carried out by applying the sweetener on a column of synthetic macroreticular resin, e.g., HP-10 or HP-20, products of Mitsubishi Chemical Industries Limited, Tokyo, Japan, or Amberlite XAD-2 or XAD-7, products of Rohm & Haas Company, Philadelphia, Pa., U.S.A., whereby the glycyrrhizin compounds are adsorbed thereon, and a large amount of free saccharides are eluted from the resin, selectively. The adsorbed glycyrrhizin compounds are eluted from the resin as follows: α-Glycosyl glycyrrhizin is eluted by washing the resin with dilute alkali solution and/or water, and charging thereto a relatively small amount of aqueous organic solvent, e.g., aqueous methanol or ethanol; and intact glycyrrhizin is eluted by charging the column with an additional amount of solvent of the same or increased concentration, after the elution of the α-glycosyl glycyrrhizin. The resultant eluate with high α-glycosyl glycyrrhizin content is then distilled to remove organic solvent, and concentrated to an appropriate level to obtain a syrup sweetener, which may be, if necessary, pulverized into powder.

Although exact estimation of the sweetening power of the sweetener containing α-glycosyl glycyrrhizin is difficult because its sweetness is quickly expressed in comparison with that of conventional glycyrrhizin sweetener, compared at the points when respective maximum sweetnesses are expressed the sweetening power of the former corresponds to that expected from the amount of glycyrrhizin solid used as a material.

Even when orally ingested without further processings, the taste quality of the present sweetener is very pleasant, mild, and non-lingering because it is almost free from undesirable bitter-, astringent-, lingering-, and harsh tastes.

Additionally, since sedimentation and gelatinization of the sweetener containing α-glycosyl glycyrrhizin under acidic conditions are extremely suppressed, the sweetener should find various uses in sweetening and seasoning low-pH food products.

It was also confirmed that the sweetener containing α-glycosyl glycyrrhizin in syrup form is extremely handleable due to its much lower foamability than conventional glycyrrhizin sweetener.

The powder sweetener containing α-glycosyl glycyrrhizin is a solid solution, wherein respective α-glycosyl glycyrrhizin compounds co-melt therein. Accordingly, the solubility of the sweetener in water is so unlimitedly high that the powder sweetener dissolves instantly in water to give a paste or syrup of high concentration.

The sweetener containing α-glycosyl glycyrrhizin can be used intact for seasoning food products. Prior to the use, the sweetener may be admixed, if necessary, with other sweetener(s), e.g., corn syrup, glucose, maltose, isomerized sugar, Coupling Sugar (Registered Trade Mark of Hayashibara Company, Limited, Okayama, Japan), sucrose, honey, maple sugar, sorbitol, maltitol, lactitol, dihydrocharcone, L-asparatyl phenylalanine methyl ester, saccharin, glycine, alanine, glycyrrhizin, stevioside, α-glycosyl stevioside or "α-G-Sweet" (Registered Trade Mark of Toyo Sugar Refining Company, Limited, Tokyo, Japan); organic acids or their salts, such as citric acid or malic acid; amino acids or their salts, such as glutamic acid or aspartic acid; fillers, such as dextrin, starch or lactose; flavor; and/or coloring agents.

The powder sweetener can be used intact, or, if necessary, prepared into granule, cube or tablet with admixing thereto of filler and/or vehicle.

The concentration of the sweetener in liquid form may be freely controlled to meet final uses.

As described hereinbefore, since the sweetening power of α-glycosyl glycyrrhizin almost corresponds to that of the amount of glycyrrhizin solid used as a material, the sweetening power of the sweetener would be dependent upon the weight ratio of amylaceous substance versus glycyrrhizin used in the enzymatic reaction.

If the ratio is about 100, the sweetening power of the resultant sweetener on dry solid basis is generally comparable to that of sucrose.

If the ratio is higher than about 100, the sweetening power of the resultant sweetener on dry solid basis is generally lower than that of sucrose. Accordingly, such sweetener with lower sweetening power would find use as a substituent of sucrose to impart to food products in general and drugs with appropriate texture, e.g., thickness, viscosity, body, and/or the like.

On the contrary, if the ratio is lower than about 100, the sweetening power of the resultant sweetener on dry solid basis is generally higher than that of sucrose. Since the lower the ratio the higher the sweetening power of the resultant sweetener would be, removal of free saccharides from the sweetener will increase its sweetening power to about 50–100-fold that of sucrose. In food products, the amount of sucrose used to sweeten them to a certain level can be greatly replaced with the use of such sweetener with high sweetness; thus, a significant calorie-reduction of sweetened food products is readily attainable therewith. Strictly, the sweetener containing α-glycosyl glycyrrhizin is advantageously feasible as a sweetener itself, or to sweeten health- and dietary-foods, including low-caloric foods, for those whose calorie-intakes are restricted, e.g., diabetics or obese persons.

Furthermore, the sweetener is favorably usable as a low-cariogenic sweetener because it is less fermentable by oral dental-caries causative microorganisms; for example, low-cariogenic food products, such as confectioneries including chewing gum, chocolate, biscuit, cookie, toffee and candy; and soft drinks including cola drinks, cider, juice, coffee and yogurt drinks. In addition to the above described uses, the sweetener is favorably usable for sweetening drugs and cosmetics, e.g., gargle or dentrifice, with much less fear of causing dental-caries.

Additionally, the taste of the present sweetener containing α-glycosyl glycyrrhizin well harmonizes with the sour-, salty-, bitter-, astringent- and/or delicious tasting substances used in various food products, as well as being highly heat- and acid-resistant. Thus, it is favourably usable for seasoning various food products, in general, in addition to the hereinbefore described special uses; for example, seasonings, such as soy sauce, soy sauce powder, soy paste, soy paste powder, dressings, mayonnaise, vinegar, powder vinegar, extracts for Chinese-style foods, sauce, catsup, curry roux, extracts for stew and soup, mixed seasoning, and table syrup; bakery products and confectioneries, such as rice cake, jerry, castella, bread, biscuit, cracker, cookie, pie, pudding, butter cream, custard cream, shoux cream, waffle, sponge cake, doughnut, chocolate, chewing gum, toffee and candy; frozen-desserts, such as ice-cream and sherbet; preserved fruits; syrups; pastes, such as flour paste, peanut paste and fruit paste; preserved foods, such as jam, marmalade, and those of fruit and vegetable; pickles and pickled products; meat products, such as ham and sausage; fish-meat products, such as ham and sausage; daily dishes, such as potato salad; bottled and canned foods, such as those of fish-meat, meat, fruit and vegetable; soft drinks, such as coffee, cocoa, juice, carbonated drinks, sour milk beverage, and yogurt drinks; liquors, such as brandy, whisky and wine; and convenient foods, such as those of pudding, hot cake, juice and coffee.

Furthermore, the sweetener containing α-glycosyl glycyrrhizin is favorably usable for sweetening and improving taste qualities of feeds and pet foods for domestic animal or fowl, honey bee, silk worm or fish, as well as sweetening and improving the taste qualities of tobacco, dentrifice, lipcream, lipstick, drug for internal administration, troche, cod liver oil drop, cachou, gargle, oral refreshing agent and the like, regardless of their final forms, e.g., solid, paste, or liquid.

In addition to the uses in food products, the sweetener would find the same medical uses as in the case of crude drug "Licorice extract" or "KANZO": it is usable in anti-inflammatory, antidiarrheal, expectorants, or cough medicine, e.g., cough syrup, or anti-asthma tablet.

As to the method by which the sweetener containing α-glycosyl glycyrrhizin is prepared into, or added to food products, feeds, pet foods, cosmetics or drugs, any method can be employed in the invention so far as the products can be prepared with, or have added, the sweetener before completion of their processing: for example, mixing, kneading, dissolving, soaking, permeating, spraying, coating, and injecting.

The following EXPERIMENTs explain the production and properties of the sweeteners containing α-glycosyl glycyrrhizin usable in the invention.

EXPERIMENT 1

Preparation of the sweeteners 1-1. Preparation of glucanotransferase

*Bacillus stearothermophilus* FERM-P No. 2222 was inoculated in 10 liters of a sterilized liquid medium, consisting of 2 w/v % soluble starch, 1 w/v % ammonium nitrate, 0.1 w/v % $KH_2PO_4$, 0.05 w/v %

MgSO$_4$.7H$_2$O, 0.5 w/v % corn steep liquor, 1 w/v % CaCO$_3$ and water, and cultivated therein at 50° C. for three days under aeration and agitation conditions.

After completion of the cultivation, the culture broth was centrifuged, and the resultant supernatant was added with ammonium sulfate to give a saturation degree of 0.7 and also to effect salting-out. The enzyme preparation thus obtained contained about 80,000 units of cyclodextrin glucanotransferase (E.C. 2.4.1.19).

One unit of cyclodextrin glucanotransferase activity is defined as the amount of enzyme that completely eliminates the iodine-colorization of 15 mg soluble starch upon enzymatic reaction at 40° C. for 10 minutes under the following conditions. To 5 ml of a 0.3 w/w % soluble starch solution in 0.02 M acetate buffer (pH 5.5), containing $2 \times 10^{-3}$ M calcium chloride, is added 0.2 ml of a dilute enzyme solution, and the mixture is then incubated at 40° C. for 10 minutes. Thereafter, 0.5 ml of the reaction mixture is added to 15 ml of 0.02 N sulfuric acid to suspend the enzymatic reaction, and the mixture is admixed with 0.2 ml of 0.1 N I$_2$-KI solution to effect iodine-colorization. Then, the absorbance of the mixture is determined at a wave length of 660 nm.

1-2. Enzymatic reaction

After dissolving 100 g "pure-Glycimin", a commercially-available purified glycyrrhizin, Registered Trade Mark of Maruzen Kasei Company, Limited, Onomichi-shi, Hiroshima-ken, Japan, and 500 g of maltodextrin, D.E., 30, in five liters of water while heating, the resultant mixture solution was cooled to 60° C., and adjusted to pH 6.0. Then, to the solution was added the cyclodextrin glucanotransferase, obtained in EXPERIMENT 1-1, in an amount of 5,000 units, and the mixture was incubated at pH 6.0 and 60° C. for 24 hours to effect enzymatic reaction.

After completion of the reaction, the reaction mixture was kept at 95° C. for 10 minutes to inactivate the enzymatic activity present therein, and the resultant, Sample No. 3 in TABLE 1, was subjected to filtration. The filtrate was then concentrated in vacuo at a temperature below 70° C., and the concentrate was prepared into the powder sweetener, Sample No. 4 in TABLE 1.

Samples No. 1 and No. 2, controls, were prepared by dissolving, similarly as above, 100 g of the purified glycyrrhizin together with or without 500 g maltodextrin in 5 liters of water while heating, and incubating the resultant mixture in the absence or presence of a thermally-preinactivated 5,000 units of the cyclodextrin glucanotransferase.

Respective formulations of the Samples are given in TABLE 1.

TABLE 1

|  | Sample No. 1* | Sample No. 2* | Sample No. 3** | Sample No. 4** |
| --- | --- | --- | --- | --- |
| Formulation | Glycyrrhizin 100 g | Glycyrrhizin 100 g + Maltodextrin 500 g + Thermally-preinactivated 5,000 units of the enzyme | Glycyrrhizin 100 g + Maltodextrin 500 g + Active 5,000 units of the enzyme | Glycyrrhizin 100 g + Maltodextrin 500 g + Active 5,000 units of the enzyme |

Note:
*control; and
**present invention.

EXPERIMENT 2

Organoleptic test on the sweeteners

Based on the results of a preliminary test on the sweetening power of the sweeteners, aqueous solutions of the sweeteners, exhibiting a sweetness comparable to that of 10% aqueous sucrose solution, were prepared.

The organoleptic test was carried out at 25° C. with 20 panel members, and, by the panel, the most desirable and the most undesirable sweeteners were chosen along with comments on their taste qualities. The results are given in TABLE 2.

The organoleptic results as shown in TABLE 2 confirm that while Samples No. 1 and No. 2 are inferior in taste quality, Samples No. 3 and No. 4 are excellent sweeteners because their taste qualities are almost comparable to that of sucrose.

As described above, since unlike conventional glycyrrhizin or mixture thereof containing other saccharide(s), the present sweetener has a pleasant, mild sweetness which is comparable to that of sucrose, and which does not linger together with any undesirable tastes, it can be readily ingested without further processings.

TABLE 2

| Judgement | Sample No. 1* | Sample No. 2* | Sample No. 3** | Sample No. 4** |
| --- | --- | --- | --- | --- |
| Most desirable | 0 | 0 | 10 | 10 |
| Most undesirable | 11 | 9 | 0 | 0 |
| Organoleptic properties | Taste quality: sweet taste, but undesirable bitter-, astringent-, and harsh tastes and medicinal odor. Expression of sweetness: delayed, and lingering together with the above undesirable tastes to give an unpleasant after-taste. Intact use is unrecommendable. | | Taste quality: desirable sweet with neither undesirable taste nor medicinal odor. Expression of sweetness: rapid, and non-lingering. Advantageously usable without | |

TABLE 2-continued

| Judgement | Sample No. 1* | Sample No. 2* | Sample No. 3** | Sample No. 4** |
| --- | --- | --- | --- | --- |
| | | | further processings. | |

Note:
*control: and
**present invention.

EXPERIMENT 3

Identification of α-glycosyl glycyrrhizin compounds

An aqueous solution, obtained by dissolving 15 g of Sample No. 4 in 100 ml water, was applied on a column, packed with 100 ml of HP-20, a commercially-available synthetic macroreticular resin, a product of Mitsubishi Chemical Industries Limited, Tokyo, Japan, and the column was then washed with sufficient water to remove the free saccharides therefrom. Thereafter, 300 ml of 50 v/v % aqueous methanol was charged thereto to elute the adsorbed glycyrrhizin compounds including α-glycosyl glycyrrhizin, and the resultant eluate was concentrated, dried and pulverized to obtain about 2.5 g of a powder sweetener (Sample No. 5).

Sample No. 5 was a colorless, odorless, neutral substance with a mild sweetness, and readily soluble in the mouth. Under acidic conditions, Sample No. 5 effected much less gelatinization than intact glycyrrhizin.

Sample No. 5 was soluble in low molecular weight alcohols, e.g., methanol, ethanol or n-propanol, but slightly in chloroform or ether.

Infrared analysis of Sample No. 5 was carried out by conventional method using KBr tablet. FIG. 1 shows the infrared spectrum of Sample No. 5, where the infrared absorption peak characteristic for an α-glycosyl linkage is observed at about 840 $cm^{-1}$, but not in that of intact glycyrrhizin.

An aqueous solution, obtained by dissolving a small portion of Sample No. 5 in a minimal amount of water, was subjected to an enzymolysis by a crystalline glucoamylase (E.C. 3.2.1.3) in 0.02M acetate buffer (pH 5.0) at 50° C. In the course of enzymolysis, small amounts of the reaction mixture were collected periodically, and spotted on "Kieselgel F 254", a commercially-available thin-layer plate, a product of Merck & Company, Incorporation, Rahway, N.J., U.S.A. The thin-layer plate was subjected to an ascending development using a mixture solution of ethyl acetate, methanol and water (2.5:1:1). After air-drying the thin-layer plate, a series of new spots corresponding to glycyrrhizin compounds were identified by UV-irradiation, and then developed by spraying thereto a developing agent, consisting of 5 w/v % vanillin and 50 v/v % methanolic sulfuric acid. Sample No. 5, and Sample No. 1 and D-glucose, used as control, were spotted and developed on the same thin-layer plate.

The thin-layer chromatographic analysis on Sample No. 5 gave a series of distinguishable spots at $R_f$ 0 66, 0.60, 0.57, 0.54, 0.51, 0.48, 0.44 and 0.34, and undistinguishable spots at $R_f$ 0.22 and 0.11, in addition to $R_f$ 0.70 glycyrrhizin spot which was also found in the thin-layer chromatography of Sample No. 1. Similarly as in the case of glycyrrhizin, the new spots were all identified by fluorescence upon UV-irradiation, and turned blue by spraying the developing agent.

An experiment, wherein Sample No. 5 was subjected to the action of glucoamylase, and small amounts of the reaction mixture were collected periodically, and analyzed similarly as above by chromatographic procedure, confirmed that the new spots were hydrolyzed gradually with the reaction time, and finally gave a blue $R_f$ 0.70 spot and greenish brown $R_f$ 0.57 spot corresponding to glycyrrhizin and D-glucose respectively.

The above experimental results suggest that the new spots of $R_f$ 0.66, 0.60, 0.57, 0.51, 0.48, 0.44, 0.34, 0.22 and 0.11 correspond to α-glycosyl glycyrrhizin compounds wherein one or more α-glucosyl residues are bound to the glycyrrhizin residues via α-glycosyl linkages.

Accordingly, Sample No. 5 is a mixture of a small amount of unreacted glycyrrhizin, and hitherto-unknown $R_f$ 0.66, 0.60, 0.57, 0.54, 0.51, 0.48, 0.44, 0.34, 0.22 and 0.11 compounds, all newly-formed by the enzymatic action of cyclodextrin glucanotransferase.

An experiment using a partially-purified α-glucosidase extracted from pig liver was carried out, and confirmed that the newly-formed compounds are also hydrolyzed by the enzyme into glycyrrhizin and D-glucose. This confirmation suggests that upon ingestion into human or animal, the compounds readily hydrolyze in vivo into glycyrrhizin and D-glucose.

Like Samples No. 3 and No. 4 in EXPERIMENT 2, Sample No. 5 readily expresses its mild sweetness without lingering—or other undesirable tastes or medicinal odor, and has an excellent taste quality comparable to that of sucrose; thus, it is favorably feasible as a sweetener for the purpose of the invention.

From the above descriptions, it is concluded that removal or elimination of the disadvantages of conventional glycyrrhizin, which is one of the present objectives, is attainable by subjecting an aqueous solution, containing glycyrrhizin and amylaceous substance, to the enzymatic action of cyclodextrin glucanotransferase to form hitherto-unknown α-glycosyl glycyrrhizin compounds.

Several embodiments of the invention are disclosed hereinafter.

EXAMPLE 1

Sweetener

*Bacillus megaterium* FERM-P No. 935 was inoculated in 5 liters of a fresh medium of the same composition as in EXPERIMENT 1—1, and then cultivated therein at 28° C. for three days under aeration and agitation conditions.

After completion of the cultivation, the culture was centrifuged to obtain a supernatant which was then added with ammonium sulfate to give a saturation degree of 0.7. Thereafter, the resultant was further subjected to centrifugation, followed by harvest of the precipitate.

The precipitate contained about 300,000 units of cyclodextrin glucanotransferase (E.C. 2.4.1.19) as defined in EXPERIMENT 1—1

To a 30 w/w % corn starch suspension was added at pH 6.0 a commercially-available liquefying enzyme in an amount of 0.2% per corn starch solid, and the starch was liquefied continuously at a temperature of 95°–98° C. The enzymatic liquefaction was continued at 90° C. until the D.E. of the liquefied starch solution reached 20, and the solution was then heated to inactivate the enzymatic activity therein.

To the liquefied starch solution was added "pure-Glycimin", a commercially-available purified glycyrrhizin product, Registered Trade Mark of Maruzen Kasei Company, Limited, Onomichi-shi, Hiroshima-ken, Japan, to give a weight ratio of glycyrrhizin versus starch partial hydrolysate of 1:3, and the mixture was cooled to 50° C. Thereafter, the mixture was added with the cyclodextrin glucanotransferase, obtained above, in an amount of 10 units per g starch solid, and kept at 50° C. and pH 5.5 for 48 hours to effect enzymatic reaction.

After completion of the reaction, the reaction mixture was heated to inactivate the enzymatic activity therein, and the resultant was filtrated. Then, the filtrate was added with "Neucillin", a commercially-available $SiO_2.Al_2O_3.MgO$ powder, Registered Trade Mark of Fuji Chemical Industry Incorporation, Limited, Toyama-ken, Japan, in an amount of 0.3% per material starch solid, and the mixture was kept for 30 minutes under gentle stirring conditions. After filtration of the mixture, the resultant filtrate was concentrated in vacuo, dried, and pulverized to obtain a powder sweetener in the yield of about 95% against the starting material solid.

The powder sweetener, obtained in this EXAMPLE, is easily handleable due to its low hygroscopicity. Since its solubility in water is extremely high, a large amount of the sweetener dissolves quickly in water, even of low temperature, to give a paste or syrup of high concentration.

The sweetening power of the sweetener on dry solid basis is about 25-fold higher than that of sucrose, and its taste is very desirable, but non-lingering.

Accordingly, the sweetener is favorably usable in any case where sweetening is required, especially, to prepare low-cariogenic- or low-caloric sweetener.

EXAMPLE 2

Sweetener

After dissolving 100 g of trisodium glycyrrhizinate, purchased from Tokyo Kasei Kogyo Company, Limited, Tokyo, Japan, and 500 g of β-cyclodextrin in 5 liters of water while heating, the solution was cooled to 60° C., followed by pH-adjustment to 5.5.

To the solution was added a cyclodextrin glucanotransferase, obtained similarly as in EXPERIMENT 1—1, in an amount of 100 units per g β-cyclodextrin solid, and the mixture was then kept at 60° C. and pH 5.5 for 24 hours to effect enzymatic reaction.

After completion of the reaction, the reaction mixture was heated to inactivate the enzymatic activity therein, followed by filtration of the resultant. Then, the filtrate was added with 2 g of "M-511", a commercially-available magnesium oxide powder, a product of Hokkaido Soda Company, Limited, Tokyo, Japan, and the mixture was kept for 30 minutes under gentle stirring conditions, followed by filtration of the mixture. Thereafter, the filtrate was applied on a column, packed with 4 liters of XAD-7, a commercially-available synthetic macroreticular resin, a product of Rohm & Haas Company, Philadelphia, Pa., U.S.A., and the column was washed with sufficient water to remove the free saccharides therefrom. Then, 10 liters of a 50 v/v % aqueous methanol was charged thereto to elute the adsorbed glycyrrhizin compounds therefrom. The eluate, containing α-glycosyl glycyrrhizin, was concentrated, and pulverized to obtain about 150 g of a powder sweetener.

Identification of the sweetener was carried out similarly as in Sample No. 5 in EXPERIMENT 3 using the thin-layer plate to obtain the following results: On the thin-layer plate, a series of distinguishable new spots were found at $R_f$ 0.67 and 0.59, and undistinguishable large spots from the origin to $R_f$ 0.26, as well as a small glycyrrhizin spot at $R_f$ 0.70, confirming that the new spots were formed by the enzymatic action of cyclodextrin glucanotransferase.

Also, it was confirmed that like Sample No. 5, the new spot compounds were hydrolyzed by glucoamylase into glycyrrhizin and D-glucose.

The sweetener, obtained in this EXAMPLE, has an about 60-fold higher sweetening power than sucrose on dry solid basis, and its taste is very desirable, but non-lingering. Accordingly, like the sweetener in EXAMPLE 1, the sweetener is favorably usable for sweetening various types of food products, as well as in a low-cariogenic- and low-caloric sweetener.

EXAMPLE 3

Sweetener

After dissolving 100 g "Licoghen", a crude yellow brown glycyrrhizin product with a glycyrrhizin content of only about 25%, Registered Trade Mark of Maruzen Kasei Company, Limited, Onomichi-shi, Hiroshima-ken, Japan, and 100 g of a maltodextrin, D.E., 18, in three liters of water while heating, the solution was cooled to 60° C., and adjusted to pH 5.5. Thereafter, to the solution was added the cyclodextrin glucanotransferase, obtained in EXPERIMENT 1—1, in an amount of 3,000 units, and the mixture was kept at 60° C. and pH 5.5 for 44 hours to effect enzymatic reaction. After completion of the reaction, the reaction mixture was heated to inactivate the enzymatic activity therein, followed by filtration of the resultant. Then, the filtrate was added with 5 g of "M-511", a commercially-available magnesium oxide powder, a fresh powder of the same composition as used in EXAMPLE 2, and the mixture was then kept for 20 minutes under gentle stirring conditions, followed by filtration of the mixture. The filtrate was concentrated in vacuo to obtain a pale yellow liquid sweetener with a moisture content of 30% in the yield of about 97% against the starting material solid.

In this EXAMPLE, much more taste-improvement of the glycyrrhizin was attained than in the case using a purified glycyrrhizin product. The sweetener is of sweetening power about 4-fold higher than that of sucrose, and favorably usable for sweetening various types of food products, cosmetics, and drugs.

Although in this EXAMPLE, complete removal of the incorporated colored impurities was quite difficult, the sweetener is much more favorably usable for sweetening certain food products, wherein a slight colored substance is negligible, in comparison with any conventional sweetener containing glycyrrhizin. For example, the use of the sweetener enables low-cost production of various food products, e.g., seasonings, such as soy sauce, sauce, soy paste, mayonnaise, and extract for soup; pickles and pickled products; confectioneries, such as chocolate, cocoa, chewing gum, pudding and candy; preserved foods; and sour milk beverage.

EXAMPLE 4

Sweetener

A sweetener mixture was prepared by dissolving 10 g of a powder sweetener, obtained similarly as in EXAMPLE 1, in 1 kg of "Mabit", a hydrogenated high maltitol syrup, Registered Trade Mark of Hayashibara Company, Limited, Okayama, Japan.

The sweetener mixture is excellent in taste quality with a sweetening power comparable to that of sucrose, but its calorie value is about 1/20 of sucrose. Accordingly, the sweetener is favorably usable for sweetening low-caloric food products for those whose calorie-intakes are restricted, e.g., diabetics or obese persons, in addition to its use as a table syrup.

Furthermore, the sweetener is hardly fermentable by oral dental-caries causative microorganisms, and, therefore, effects formation of neither organic acid nor water-insoluble glucan. Thus, it is favorably usable for sweetening various food products with a purpose of preventing dental caries.

EXAMPLE 5

Sweetener

Eight hundred g of glucose was homogenously admixed with 100 g sucrose and 5 g of a powder sweetener, obtained similarly as in EXAMPLE 2, and the mixture was pulverized. The resultant powder was sprayed with a small amount of water, and then prepared into cubic sweetener by applying a slightly high pressure.

The cubic product is a sweetener solid which has an excellent taste quality, sweetening power almost comparable to that of sucrose, and high solubility in cold water. A chilled solution of the sweetener is favorably usable intact as a soft drink.

It is suggested that the excellent taste quality of the sweetener is due to the synergic effect of admixing the above described three sweeteners.

EXAMPLE 6

Sweetener

A sweetener mixture was prepared by dissolving 16 g of a powder sweetener, obtained similarly as in EXAMPLE 2, in 20 ml of water, and admixing homogenously the resultant solution with 1 kg of honey.

The sweetener mixture has an about 2-fold higher sweetening power than sucrose, and is excellent in taste quality due to the incorporated honey constituent. Thus, it is favorably usable for sweetening various health- and dietary-food products, as well as improving the taste qualities of drugs.

EXAMPLE 7

Hard candy

After dissolving 60 g of a sweetener, obtained similarly as in EXAMPLE 1, in 15 kg of "Mabit", a hydrogenated high maltitol syrup, Registered Trade Mark of Hayashibara Company, Limited, Okayama, Japan, the resultant mixture was concentrated by heating in vacuo to give a moisture content of about 2% or less. The concentrate was then admixed with 150 g of citric acid, and small amounts of lemon flavor and coloring agent, and the resultant was shaped into the titled product in usual way.

The product is an extensively sweet, low-cariogenic, low-caloric hard candy.

EXAMPLE 8

Chewing gum

After softening 2 kg of gum base by heating, the gum base was added with 6 kg of a crystalline lactitol powder, 160 g of a sweetener, obtained similarly as in EXAMPLE 2, 1 kg of crystalline sorbitol powder, and small amounts of menthol and coloring agent. Thereafter, the mixture was kneaded sufficiently with the use of a roller, and the resultant was shaped into the titled product, in the usual way.

The product is a low-cariogenic, low-caloric chewing gum with excellent chewing properties and appropriate sweetness.

EXAMPLE 9

Chocolate

A composition, consisting of 40 kg cacao paste, 10 kg cacao butter, 10 kg maltose, 5 kg lactose, 20 kg whole milk, and 1 kg of a sweetener, obtained similarly as in EXAMPLE 1, was kneaded sufficiently, and the mixture was then placed in a refiner to reduce its particle size. Thereafter, the content was transferred into a conche, added with 500 g lecithin, and kneaded at 50° C. for 2 days therein. Then, the content was placed in a shaping apparatus, and solidified therein to obtain the titled product.

The product is a low-cariogenic chocolate with an excellent texture, flavor and taste quality, and free from fat- or sugar-blooming during storage.

EXAMPLE 10

Sour milk beverage

After pasteurizing 10 kg of defatted milk at 80° C. for 20 minutes, the milk was cooled to 40° C., and added with 300 g of a starter, followed by 10-hour incubation of the mixture at 35°–37° C.

After completion of the incubation, the resultant was homogenized, and added with 2 kg of a liquid sweetener, obtained similarly as in EXAMPLE 3, and 2 kg of "Coupling Sugar", Registered Trade Mark of Hayashibara Company, Limited, Okayama, Japan, and the resultant mixture was kneaded sufficiently at 80°–85° C. under gentle stirring conditions to effect pasteurization.

The mixture was cooled, admixed with a small amount of flavor, and bottled to obtain the tilted product.

The product is a low-cariogenic sour milk beverage.

EXAMPLE 11

"TSUKUDANI"

Two hundred and fifty g of tangle was treated to remove the sand stuck thereto, soaked in acid solution, and cut into squares, according to the conventional method. Thereafter, the tangle was soaked in a mixture solution, consisting of 212 ml soy sauce, 318 ml amino acid solution, 50 g powder syrup, 1 g pullulan, and 10 g of a liquid sweetener, obtained similarly as in EXAMPLE 3. While boiling, the content was added with 12 g monosodium glutamate, 8 g caramel and 21 ml "MIRIN"-a type of Japanese-style liquor, and finally boiled up to obtain the titled product, "TSUKUDANI"-a type of Japanese-style preserved food.

The product is an appetizing "TSUKUDANI" with an excellent colour, gloss, appearance, flavor and taste.

EXAMPLE 12

Pickled scallion

Five kg of raw scallion was soaked in 2.5 liters of an about 20% aqueous sodium chloride solution for three weeks. After draining off the water, the scallion was further soaked for one month in an acetic acid solution, consisting of 2.0 liters of water, 80 g of glacial acetic acid, and 80 g of sodium chloride. Thereafter, the scallion was further soaked for 10 days in a seasoning solution, consisting of 800 ml of vinegar, 400 ml of "MIRIN"-a type of Japanese-style liquor, 10 g of cayenne-pepper, and 10 g of a sweetener, obtained similarly as in EXAMPLE 2, to obtain a pickled scallion with an excellent flavor and taste.

EXAMPLE 13

Tablet

A mixture, consisting of 50 g acetyl-salicylic acid, 13 g maltose, 4 g corn starch, and 1 g of a sweetener, obtained similarly as in EXAMPLE 2, was kneaded sufficiently. Then, the mixture was shaped with the use of a tabletting machine, equipped with 20 R-punch of 12 mm diameter, into tablets of 680 mg each, 5.25 mm thick, and 8±1 kg hardness.

The tablet can be easily administrated due to its appropriate sweetness.

EXAMPLE 14

Tooth paste

A tooth paste was prepared by kneading a composition with a formulation of CaHPO$_4$, 45.0%; pullulan, 2.75%; sodium lauryl sulfate, 1.5%; glycerin, 20.0%; polyoxyethylene sorbitan mono-ester, 0.5%; antiseptic agent, 0.05%; a sweetener, obtained similarly as in EXAMPLE 2, 0.2%; and water, 30.0%, in usual way.

The product is favorably usable as a tooth paste directed to children's use due to its appropriate sweetness.

BRIEF EXPLANATION OF FIGURE

FIG. 1 is the infrared spectrum of Sample No. 5 in EXPERIMENT 3.

We claim:

1. In an orally usable product containing a sweetening or flavoring amount of a sweetening or flavoring agent, the improvement wherein said sweetening or flavoring agent comprises α-glycosyl glycyrrhizin.

2. An orally usable product in accordance with claim 1, wherein said product is selected from the group consisting of dentifrice, medicine, cosmetic, troche, cod liver oil drop, gargle and oral refreshing agent.

3. An orally usable product in accordance with claim 1, wherein the product is a food product.

4. A food product in accordance with claim 3, in liquid form.

5. A food product in accordance with claim 3, in paste form.

6. A food product in accordance with claim 3, in solid form.

7. A food product in accordance with claim 3, wherein said food product is a low-cariogenic food product.

8. A food product in accordance with claim 3, wherein said food product is a low-caloric food product.

9. A food product in accordance with claim 3, wherein said food product is a seasoning.

10. A food product in accordance with claim 3, wherein said food product is a confectionery.

11. A food product in accordance with claim 3, wherein said food product is a bakery product.

12. A food product in accordance with claim 3, wherein said food product is a beverage.

13. A food product in accordance with claim 3, wherein said food product is a sweetener.

* * * * *